United States Patent [19]

Vicario et al.

[11] 4,211,864

[45] Jul. 8, 1980

[54] DAUNORUBICIN AND DOXORUBICIN LABELLED WITH $^{14}$C AT THE 14-POSITION AND PROCESSES FOR THEIR PREPARATION

[75] Inventors: Gian P. Vicario, Novara; Sergio Penco; Federico Arcamone, both of Milan, all of Italy

[73] Assignee: Societa Farmaceutici Italia (Farmitalia Carlo Erba S.p.A.), Milan, Italy

[21] Appl. No.: 877,755

[22] Filed: Feb. 14, 1978

[30] Foreign Application Priority Data

Feb. 16, 1977 [GB] United Kingdom ............... 06372/77

[51] Int. Cl.$^2$ ............................................ C07H 15/24
[52] U.S. Cl. ................................. 536/17 A; 424/180; 536/4
[58] Field of Search ...................... 536/4, 17, 17 A, 26

[56] References Cited

U.S. PATENT DOCUMENTS

| 3,803,124 | 4/1974 | Arcamone et al. ................. 536/17 A |
| 3,945,993 | 3/1976 | Schaffner et al. ..................... 536/17 |

*Primary Examiner*—Johnnie R. Brown
*Attorney, Agent, or Firm*—Hubbell, Cohen, Stiefel & Gross

[57] ABSTRACT

[14-$^{14}$C]-daunorubicin and doxorubicin are prepared by reacting 9-desacetyl-9-formyl-N-trifluoroacetyl daunorubicin with [$^{14}$C]-diazomethane to form [14-$^{14}$C]-N-trifluoroacetyl daunorubicin from which the protecting group is removed by mild alkaline hydrolysis to afford [14-$^{14}$C]-daunorubicin which is then, in the form of the hydrochloride, reacted with bromine to form the corresponding labelled 14-bromo derivative, which, upon treatment with sodium formate leads to [14-$^{14}$C]-doxorubicin.

10 Claims, 1 Drawing Figure

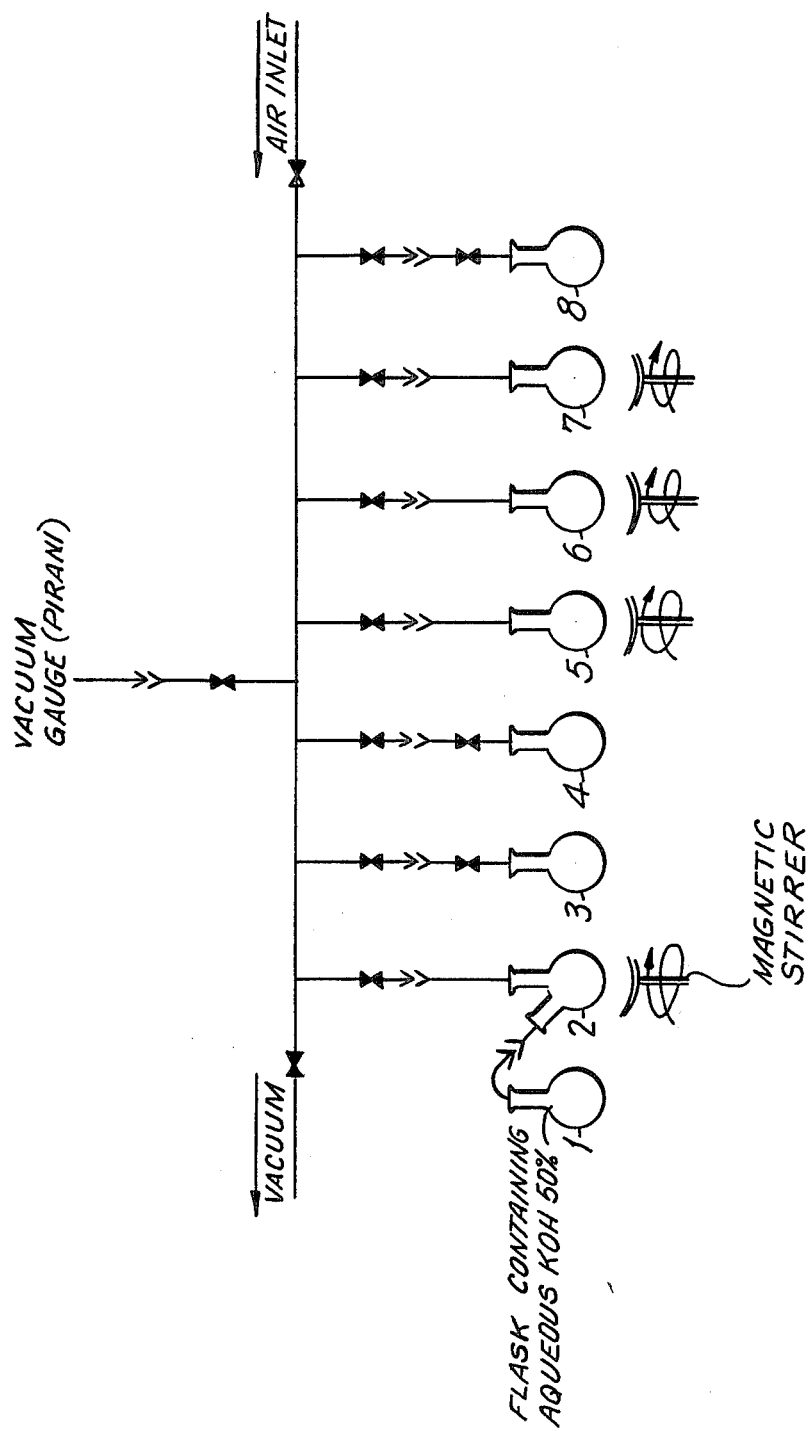

DAUNORUBICIN AND DOXORUBICIN LABELLED WITH $^{14}C$ AT THE 14-POSITION AND PROCESSES FOR THEIR PREPARATION

CROSS REFERENCE TO RELATED APPLICATIONS

This application is related to and incorporates by reference the contents of copending application Ser. No. 860,448 filed Dec. 14, 1977, owned by the unrecorded assignee hereof.

BACKGROUND OF THE INVENTION

The invention relates to the known antitumor antibiotics daunorubicin (daunomycin) and doxorubicin (adriamycin) and more specifically, to said antibiotics labelled with $^{14}C$ at the 14-position thereof and methods for preparing such labelled antibiotics.

Daunorubicin and doxorubicin are both known compounds. Moreover, daunorubicin an doxorubicin labelled with tritium ($^3H$) are also known, their preparation having been described by Carter et al, International Symposium on Adriamycin; Springer-Verlag, Berlin, p. 9, 1972. These tritiated compounds have been used for a variety of biochemical and medical studies, They are, however, of limited use because of the exchange of tritium in body fluids and the buffered solutions which are often utilized in biochemical studies.

Thus, notwithstanding the availability of tritiated daunorubicin and doxorubicin there exists a quite considerable need for daunorubicin and doxorubicin labelled with a more stable isotope and with a high specific activity.

$^{14}C$-labelled daunorubicin and doxorubicin are very important tools for studying the distribution, pharmacokinetics and metabolism of these antitumor drugs. [14-$^{14}C$]-daunorubicin and [14-$^{14}C$]-Doxorubicin have not heretofore been synthesized.

SUMMARY OF THE INVENTION

The invention provides, in one aspect thereof, a new process for preparing the heretofore unknown [$^{14}C$]-daunorubicin and doxorubicin labelled in the 14-position, in which 9-desacetyl-9-formyl-N-trifluoroacetyl daunorubicin is reacted with [$^{14}C$]-diazomethane. This reaction affords [$^{14}C$]-N-trifluoroacetyl daunorubicin from which [$^{14}C$]-daunorubicin is obtained by mild alkaline hydrolysis. To obtain [$^{14}C$]-doxorubicin, the labelled daunorubicin is first converted to the 14-bromo derivative by treatment with bromine and the resulting intermediate is hydrolyzed with sodium formate to form [$^{14}C$]-doxorubicin.

In another aspect, the invention provides the new compounds [14-$^{14}C$]-daunorubicin and doxorubicin as well as their hydrochlorides.

BRIEF DESCRIPTION OF THE DRAWING

The drawing is a schematic representation of an apparatus for conducting the process of the invention.

DESCRIPTION OF THE PREFERRED EMBODIMENTS

The chemical synthesis by which the labelled compounds of the invention are made, is based upon the reaction of 9-desacetyl-9-formyl-N-trifluoroacetyl-daunorubicin (II)[a] with diazomethane.

[a] Compound II is obtained from 13-dihydro-N-trifluoroacetyl-doxorubicin (I) by periodate oxidation of the C-13, C-14 diol described in co-pending application Ser. No. 860,448 which is owned by the unrecorded assignee hereof and the contents of which are incorporated herein by reference filed 12/14/77.

The total synthetic route is outlined in the following reaction scheme:

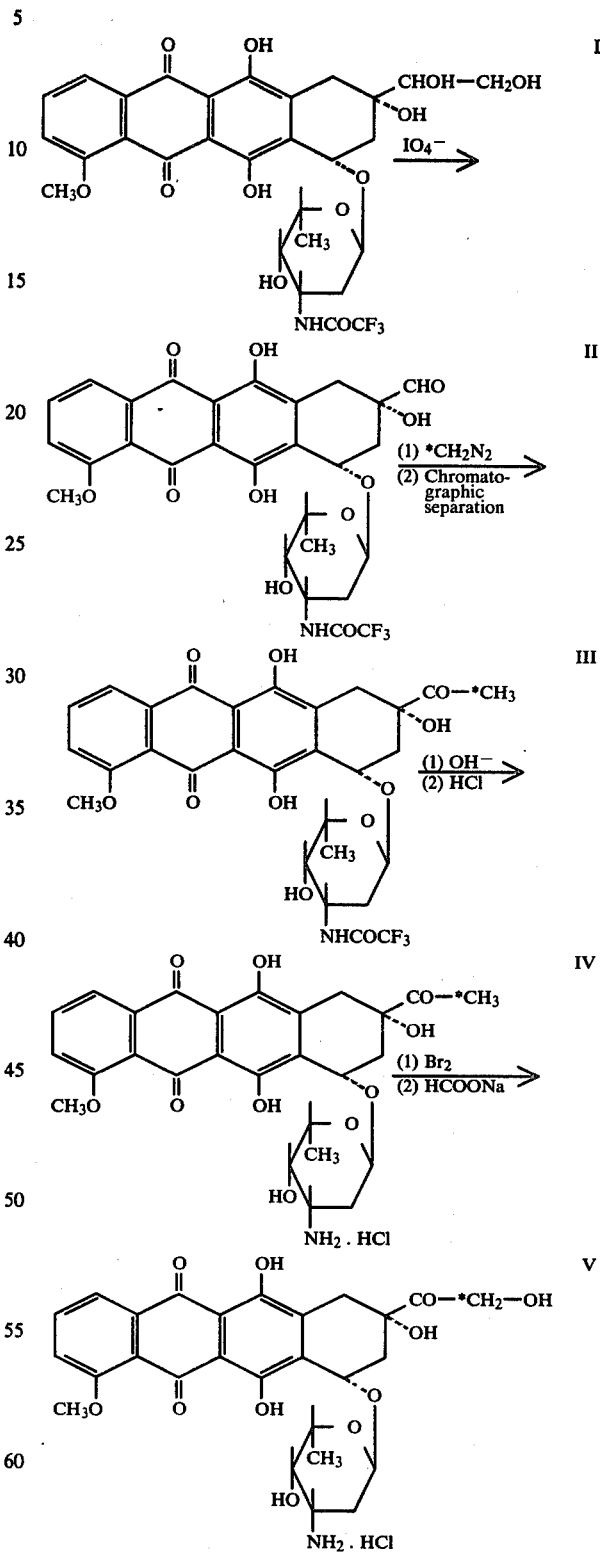

*represents $^{14}C$

The conversion of (II) to (III) is carried out using a vacuum manifold of the type represented in the drawing. Three portions of the aldehyde (II), in the solid state, are placed in flasks 5, 6 and 7 and treated, at room temperature, and under vacuum, with [$^{14}$C] diazomethane in a suitable inert organic medium such as methylene chloride and/or diethyl ether or other aprotic organic solvent. More precisely, an ethereal solution of *CH$_2$N$_2$, generated in flask 2, is distilled into flask 3 and then transferred successively into flask 4 containing an equal volume of CH$_2$Cl$_2$ or CHCl$_3$. Then the organic solution of the labelled diazomethane is transferred, by distillation, into flask 5, containing a portion of (II). At the end of the reaction (about 60 minutes at room temperature), the excess, or unreacted *CH$_2$N$_2$ is distilled into flask 6, to react with the second portion of (II). Finally, the remaining unreacted radioactively labelled diaxomethane is distilled into flask 7 where it is completely reacted with the third portion of (II). The solvents are finally recovered in flask 8. This procedure allows one to completely bind the radioactivity to (II) and therefore optimize the yield as [14-$^{14}$C]-N-trifluoroacetyldaunorubicin (III). The combined crude product from flasks 5, 6 and 7 is preferably purified before the following alkaline treatment. The purification is performed by chromatographic separation using preparative silica gel plates or a column of silicic acid and an eluent system constituted by a 4:1 (by volume) mixture of chloroform and acetone. The mild alkaline treatment of pure N-trifluoroacetyldaunorubicin (III) (performed in order to hydrolyze off the protective group) is carried out at 0°–5° C. with aqueous 0.1 N sodium hydroxide or ammonium hydroxide over a period of 30–60 minutes. The glycoside (IV) is recovered as the hydrochloride in the following manner: The alkaline solution is adjusted to pH 4.5 with 0.5 N hydrochloric acid and extracted with chloroform in order to remove the aglycones.

The solution is then brought to pH 8.5 and repeatedly extracted with chloroform. The combined chloroform extracts are evaporated to a small volume under vacuum and the stoichiometric amount of methanolic hydrogen chloride is added to give 14-$^{14}$C-daunorubicin hydrochloride (IV).

The radiochemical yield, based on [$^{14}$C]-methylamine. HCl, which is the precursor of the [-$^{14}$C]-diazomethane via N-nitroso-N-[$^{14}$C]-methylurea, is about 10%.

The preparation of [14-$^{14}$C]-doxorubicin (V) is performed in accordance with the method described in U.S. Pat. No. 3,803,124 (which is also owned by the unrecorded assignee hereof) for the chemical transformation of daunorubicin to doxorubicin. The treatment of (IV) with bromine gives the corresponding [14-$^{14}$C]-14-bromoderivative which, upon hydrolysis is converted to [14-14C]-doxorubicin (V).

The following examples are given to more fully illustrate the invention.

EXAMPLE 1

[14-$^{14}$C]-Daunorubicin (IV)

9-Desacetyl-9-formyl-N-trifluoroacetyldaunorubicin (II) (0.118 g., 0.193 mmoles) was placed in flasks 5, 6 and 7 in the following amounts: 0.035 g., 0.055 g. and 0.028 g. Then a mixture of diethyl ether-methylene chloride (1:1 v/v, 20 ml.) containing $^{14}$CH$_2$N$_2$, prepared from 940 μC of NH$_2$$^{14}$CH$_3$. HCl (0.477 mmoles, 1.97 mC/mmoles) was distilled in a vacuum manifold into flask 5 containing the first portion of (II) (0.035 g.). After 60 minutes at room temperature, with stirring, the excess $^{14}$CH$_2$N$_2$ was distilled into flask 6 containing the second portion of substrate (0.055 g.). The reaction was run as described above. Finally, the residual radioactive reagent was transferred by distillation into the third flask 7 containing 0.028 g. of (II).

The combined radioactive products (0.127 g.) were purified by preparative thin-layer chromatogaphy on silica gel plates (2 mm thick) using the solvent system chloroform-acetone (1:1 v/v) as the eluent. The band containing N-trifluoroacetyl [14-$^{14}$C]-daunorubicin was removed, quantitatively transferred into a beaker and washed with 10 ml. of 5% aqueous methanol and then with 20 ml. chloroform. The organic phase was filtered through a porous glass filter. After six washings, the silica gel was completely colorless. The combined extracts were evaporated to a residue under vacuum. The residual solid, dissolved in 20 ml. of chloroform and filtered through a paper filter was evaporated to dryness, giving 0.047 g. of (III).

This compound was identical with an authentic sample of N-trifluoroacetyldaunorubicin obtained by treatment of daunorubicin with trifluoroacetic anhydride [F. Arcamone et al, Chim. Ind. (Milan) 51, 834 (1969)]. A solution of (III) in 10 ml. of 0.1 N NaOH, after 60 minutes at 0° C. was adjusted to pH 4.5 with 0.5 N hydrochloric acid and extracted with chloroform until the extracts are colorless. Then the aqueous solution was adjusted to pH 8.5 with 0.1 N NaOH and repeatedly extracted with chloroform (20 ml.×5) until the color was transferred to the organic phase completely. The stoichiometric amount of 0.1 N methanolic hydrochloric acid was added to the combined organic extracts. Finally, the resulting red solution was evaporated at 35° C. to dryness, giving 0.030 g. of [14-$^{14}$C]-daunorubicin hydrochloride, specific activity 3.25 μC/mg. (1.832 mC/mmoles.) Following the above-outlined procedure and starting from 10 mC of NH$_4$$^{14}$CH$_3$. HCl (specific activity 19.27 mC/mmole) and 0.150 g. of aldehyde II, 44 mg. of [14-$^{14}$C]-daunorubicin hydrochloride with a specific activity of 19.18 mC/mmole were obtained (15.0% radiochemical yield).

EXAMPLE 2

[14-$^{14}$C]-Doxorubicin hydrochloride (V)

A solution of (IV) in a mixture of methanol and dioxane was treated with bromine to give the corresponding 14-bromo derivative. The following treatment with an aqueous solution of sodium formate at room temperature for 100 hours gave [14-$^{14}$C]-doxorubicin which was isolated as the hydrochloride. Following this procedure [14-$^{14}$C]-doxorubicin hydrochloride (29 mg.; specific activity 14.04 mC/mmole and 10 mg.; specific activity 6.54 mC/mmole) were obtained starting from [14-$^{14}$C;]-daunorubicin (54 mg.; specific activity 14.18 mC/mmole) with a 60.4% overall radiochemical yield.

Variations and modifications can, of course, be made without departing from the spirit and scope of the invention.

Having thus described our invention, what we desire to secure by Letters Patent and hereby claim is:

1. A process for preparing [14-$^{14}$C]-daunorubicin which comprises reacting 9-desacetyl-9-formyl-N-trifluoroacetyl-daunorubicin dissolved in an inert aprotic organic solvent, with [$^{14}$C]-diazomethane to form a reaction mixture including [14-$^{14}$C]-N-trifluoroacetyl-daunorubicin separating the [14-$^{14}$C]-N-trifluoroacetyl-daunorubicin from said reaction mixture and treating same with an aqueous base to hydrolyze off the N-trifluoroacetyl protecting group and thereby obtain [14-$^{14}$C]-daunorubicin base.

2. A process according to claim 1, wherein the inert aprotic organic solvent is methylene chloride or diethyl ether.

3. A process according to claim 1, wherein said reacting is effected under vacuum at about 20° C. for about one hour.

4. A process according to claim 1, wherein said separating is effected by preparative silica gel chromatography.

5. A process according to claim 1, wherein the aqueous base is a solution of NaOH or NH$_4$OH of about 0.1 Normality and said treating is effected for about 30–60 minutes at a temperature of about 0°–5° C.

6. A process according to claim 1, and further comprising treating the [14-$^{14}$C]-daunorubicin base methanolic HCl to convert the base to the hydrochloride.

7. A process according to claim 6, and further comprising reacting [14-$^{14}$C]-daunorubicin.HCl with bromine to form the corresponding 14-bromo derivative and hydrolyzing the 14-bromo derivative with an aqueous solution of sodium formate to obtain [14-$^{14}$C]-doxorubicin base.

8. A process according to claim 7, wherein hydrolyzing is effected for about 100 hours at about 20° C.

9. A process according to claim 7, and further comprising converting [14-$^{14}$C]-doxorubicin to the hydrochloride.

10. A compound of the formula:

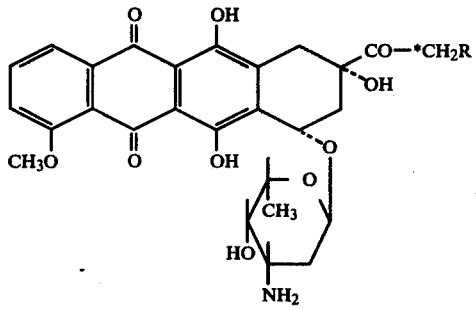

wherein R is H or OH and the symbol * indicates $^{14}$C and the hydrochlorides thereof.

* * * * *

UNITED STATES PATENT OFFICE
CERTIFICATE OF CORRECTION

Patent No. 4,211,864     Dated July 8, 1980

Inventor(s) Vicario et al.

It is certified that error appears in the above-identified patent and that said Letters Patent are hereby corrected as shown below:

Column 6, line 6: "doxorubicin" should read --doxorubicin base--

Signed and Sealed this

Third Day of March 1981

[SEAL]

Attest:

RENE D. TEGTMEYER

Attesting Officer      Acting Commissioner of Patents and Trademarks